(12) United States Patent
Robinson et al.

(10) Patent No.: US 11,214,539 B1
(45) Date of Patent: Jan. 4, 2022

(54) BIOBASED DIISOCYANATES, AND PROCESS FOR PREPARATION OF SAME

(71) Applicant: Evoco Limited, Toronto (CA)

(72) Inventors: Jason James Robinson, Toronto (CA); Juri Helmut Moebus, North York (CA); Tristan Calayan, Mississauga (CA); Guerino G. Sacripante, Oakville (CA)

(73) Assignee: Evoco Limited, Toronto (CA)

( * ) Notice: Subject to any disclaimer, the term of this patent is extended or adjusted under 35 U.S.C. 154(b) by 0 days.

(21) Appl. No.: 17/390,145

(22) Filed: Jul. 30, 2021

(51) Int. Cl.
*C07C 263/00* (2006.01)
*C08G 18/76* (2006.01)
*C07C 263/12* (2006.01)
*C08G 18/75* (2006.01)

(52) U.S. Cl.
CPC .......... *C07C 263/12* (2013.01); *C08G 18/758* (2013.01); *C08G 18/7678* (2013.01); *C08G 18/7685* (2013.01)

(58) Field of Classification Search
CPC ............... C07C 263/12; C08G 18/758; C08G 18/7678; C08G 18/7685
See application file for complete search history.

(56) References Cited

U.S. PATENT DOCUMENTS 4,597,910 A * 7/1986 Konig .................. C07C 205/37
 521/170
9,950,996 B2 * 4/2018 Wadgaonkar ...... C08G 18/3206

FOREIGN PATENT DOCUMENTS

EP          0505316    * 11/1992   ........... C07C 275/12

OTHER PUBLICATIONS

"New resin acid derivatives: diisocyanate, diurethanes, and diureides" to Gigante. Synthetic Communications, 28(4), 639-652 (1998).*

* cited by examiner

*Primary Examiner* — Michael L Leonard

(57) ABSTRACT

Biobased diisocyanates are bio-derived derived from biomass natural sources that include rosin acids. The biobased diisocyanates are of the formula 1, 2 or 3:

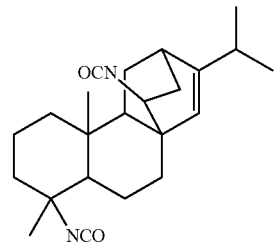

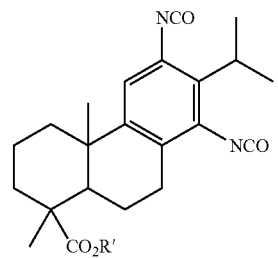

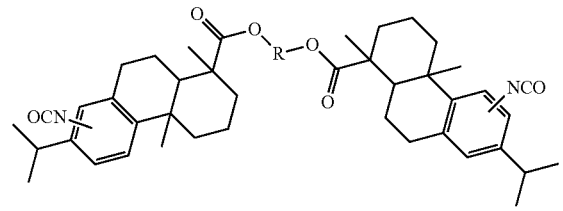

where:

R is an alkylene of from about 2 to about 12 carbon atoms, and

R' is an alkyl group of from about 1 to about 12 carbon atoms.

12 Claims, 5 Drawing Sheets where:

R is an alkylene of from about 2 to about 12 carbon atoms;

R´ is an alkyl group of from about 1 to about 12 carbon atoms.

where: R' is an alkyl group of from about 1 to about 12 carbon atoms.

where:

R is an alkylene of from about 2 to about 12 carbon atoms.

where:

R is an alkylene of from about 2 to about 12 carbon atoms.

BIOBASED DIISOCYANATES, AND PROCESS FOR PREPARATION OF SAME

This disclosure is generally directed to diisocyanates, and in particular to organic diisocyanates that are bio-derived from natural sources or derived from biomass starting materials such as rosin acids. Specifically, this disclosure further provides biobased diisocyanates of the structures 1, 2 and 3 shown in FIG. 1, and to methods for their preparation.

BACKGROUND

Polyurethanes are a large class of polymers used in a wide range of applications, such as construction, automotive, furniture, footwear, insulation, coatings, adhesives, elastomer foams, and consumer goods. Polyurethanes are produced from the polymerization reaction between polyols and/or aliphatic diols with diisocyanates. Usually, the polyols are hydroxyl-terminated oligomers or polymers, such as poly (ethylene oxide), poly (propylene oxide), poly (alkylene glycols) or polyester resin with terminal hydroxyl groups. The diisocyanates are usually selected as toluene-diisocyanate, 4,4'-methylene diphenyl diisocyanate, isophorone diisocyanate and hexamethylene diisocyanate. The properties of polyurethanes vary depending on the structure of the polymer backbone and can be tailored to have high strength and rigidity, or high flexibility and toughness. When a polyol (and or aliphatic diol) reacts with the diisocyanate, it forms a linear, thermoplastic polymer. If crosslinking agents are utilized, such as diethanol amine, polyhydric alcohol or polyols with three or more hydroxyl moieties and/or poly-isocyanates with three reactive isocyanate groups, the varying degrees of crosslinking in the polyurethane product can be tailored to achieve a rigid, cross-linked, thermosetting polyurethane. Additionally, additives are commonly added during the reaction of the polyurethane to improve certain properties, such as chain-extending agents, blowing agents, surfactants, fillers, plasticizers, pigments and flame retardants. Blowing agents will create a polyurethane foam, and surfactants will control the bubble formation and, therefore, the cell formation of the foam. In general, fillers increase stiffness, plasticizers reduce hardness and pigments add colour to the material. Additionally, there are many aromatic and aliphatic poly-isocyanates; however, the most important of these being toluene diisocyanate (TDI) and 4,4'-methylene diphenyl diisocyanate (MDI), which are used in the production of around 95% of all polyurethanes. TDI is generally used in the production of soft, flexible foams for cushioning, whereas MDI is used in the production of more versatile, rigid polyurethanes. Other less common diisocyanates such as the aliphatic hexamethylene diisocyanate or cycloaliphatic isophorone diisocyanates are known and utilized for polyurethane compositions useful in specialty applications, such as enamel paints and coatings which are resistant to abrasion or degradation by ultraviolet light. The main components of the polyurethane, namely the polyols and the diisocyanates, are mainly derived from petrochemicals, and their production contributes heavily towards greenhouse gasses that negatively impact the environment. There is an overall need for polyols and diisocyanates that are based on renewable resource materials derived primarily from a biomass such that there is less dependency on fossil fuels, which accelerate climate change.

Examples of polyols derived from biobased chemicals are known. For example, U.S. Pat. No. 10,934,384 describes selection of biobased polyester-polyols used for producing polyurethane resins. The polyurethanes are obtained from biobased polyols, additives and petrochemically derived diisocyanate such as MDI, to result in an overall biobased content of from about 70 to about 85% by weight of the corresponding polyurethane composition.

Rosin based diisocyanates are also known, such as those described by Bingham and Marvel in "Preparation and Polymerization of a Diisocyanate from the Diels-Alder Adduct of Levopimaric Acid", Journal of Polymer Science: Part A-1, 10, p. 921 (1972), in which the Diels-Alder adduct of levopimaric acid and acrylic acid is converted to the ethyl ester diisocyanate.

In co-pending U.S. application Ser. No. 17/245,807, there are described biobased diisocyanates derived from 3-pentadecyl phenol, which is derived from cardanol harvested from cashew nutshell liquid food waste.

U.S. Pat. No. 9,950,996 describes biobased aromatic diisocyanates, wherein the starting materials are namely, bis(4-isocyanato-2-methoxyphenoxy)alkane and bis(4-isocyanato-2, 6-dimethoxyphenoxy) alkanes and are synthesized from vanillic acid/syringic acid which have their origin in bio-resources such Lignin. The aromatic biobased diisocyanates are analogous in structure to petrochemically-derived MDI.

U.S. Pat. Nos. 8,044,166, 9,404,132 and 9,765,369 describe a process for making 1,5-pentylene diisocyanate from bioderived 1,5-pentane diamine obtained from enzymatic decarboxylation of L-lysine. The aliphatic biobased diisocyanates are analogous in structure to oil-derived hexamethylene diisocyanates.

Cawse et al., "Polymers from renewable sources", Die Makromolekulare Chemie, 185 (4) p. 697 (1984), describes the synthesis of furan diisocyanates from methyl furoate and furfuryl-amine which are bioderived from maize, oats and husks. The aromatic biobased diisocyanates are analogous in structure to MDI, and furthermore are obtained from a food-based bioresource.

There is a need to provide polyurethane compositions wherein the biobased content is, for example, from about 95% to about 100% by weight of the polyurethane composition. While the objective is to increase the renewable content of the polyurethane foam, it is also desirable to maintain or improve the performance properties of the polyurethane composition. To achieve a high renewable content of the polyurethane foam, there is a need for biobased polyols, biobased additives, biobased fillers, biobased colorants and biobased diisocyanates.

There is also a need for biobased diisocyanates that are aromatic and analogous in structure to TDI and MDI. Furthermore, there is a need for biobased diisocyanates that are primarily derived from non-food-based biomass or food-waste biomass.

Furthermore, there is a need to provide biobased aromatic diisocyanates derived from food-waste or non-food biomass, with biobased polyols, fillers, additives and colorants for the production of polyurethane composition for many applications, wherein the biobased content is from about 95% to about 100% by weight of the polyurethane composition.

These and other needs can be achievable with the biobased diisocyanates of the present disclosure.

SUMMARY

Illustrated herein is a biobased diisocyanate that is bio-derived from natural sources or derived from biomass starting materials comprised of rosin acids that are obtained from pulp by-product (tall oil), gum, or wood and that are easily extracted, inexpensive, and sustainable with worldwide production in excess of 1.2 million tons annually The rosin acid mixture is mainly composed of abietic acid depending on its source, and is converted with other isomers such as neoabietic, plausteric, and levopimaric acids to a rosin diacid (4) utilizing acrylic acid (FIG. 2) as disclosed by Halbrook et al., in "Preparation of Modified Rosin", Ind. Eng. Chem. Prod. Res. Develop., Vol. 1 1, No. 2, 1972. Disproportionation (aromatization) of the rosin diacid yields the dehydroabietic acid (5) (FIG. 2), as disclosed in U.S. Pat. No. 6,087,318.

The present invention provides biobased diisocyanates as illustrated in FIG. 1, wherein each of structure 1 and 2 is an aromatic diisocyanate which is analogous in structure to TDI, and wherein structure 3 is a bis-aromatic diisocyanate which is analogous in structure to MDI. The biobased diisocyanates are primarily derived from non-food-based biomass or food-waste biomass and are from about 70 to about 100% biobased by weight.

The biobased diisocyanate is of the formula 1, 2 or 3 as illustrated in FIG. 1, wherein R is an alkylene of from about 2 to about 12 carbon atoms and R' is an alkyl group of from about 1 to about 12 carbon atom such as methyl, ethyl, propyl, butyl, etc.

The biobased diisocyanate of formula 1 is a rosin diisocyanate and can be named in accordance with IUPAC nomenclature as 8,11-diisocyanato-2-isopropyl-4b,8-dimethyl-4,4a,4b,5,6,7,8,8a,9,10-decahydro-3H-3,10a-ethanophenanthrene, as depicted in FIG. 1. The biobased diisocyanate of formula 2, may be selected from the group consisting of alkyl 12,14-diisocyanato dehydro-abietate, wherein the alkyl group R' is any of methyl, ethyl, propyl, butyl, pentyl, hexyl, heptyl, octyl, nonyl, decyl, undecyl and dodecyl, as depicted in FIG. 1. The biobased diisocyanate of formula 3, may be selected from the group consisting of bis (isocyanato-dehydro-abietate) alkane, as depicted in FIG. 1.

A process for the preparation of the biobased diisocyanate of formula 1, may begin with an initial step of subjecting a mixture of rosin acids, such as gum rosin, tall oil rosin and/or wood rosin, with acrylic acid and hydroquinone to yield a rosin diacid 4. This may then be followed by (i) esterification of rosin diacid 4 to rosin diester 5 (ii) conversion of the rosin diester 5 to rosin di-hydrazide 6, (iii) followed by the preparation of rosin di-azide 7 from the rosin di-hydrazide 6 with (iv) subsequent heating via the Curtius rearrangement to the rosin diisocyanate 1 (FIG. 2).

A process for the preparation of the biobased diisocyanate of formula 1, may alternatively begin with an initial step of subjecting a mixture of rosin acids, such as gum rosin, tall oil rosin and/or wood rosin, with acrylic acid and hydroquinone to yield a rosin diacid 4. This may then be followed by (i) anhydridification of the rosin diacid 4 to rosin di-(ethyl carbonic) anhydride 8 (ii) conversion of the rosin di-(ethyl carbonic) anhydride 8 to rosin di-azide 7, (iii) with subsequent heating via the Curtius rearrangement to the rosin diisocyanate 1 (FIG. 2).

A process for the preparation of the biobased diisocyanate of formula 2, may comprise the steps of: (i) esterification of dehydro-abietic acid 9 to alkyl dehydro-abietate 10, (ii) di-nitration of the alkyl dehydro-abietate 10 to alkyl di-nitro dehydro-abietate 11, (iii) reduction of the alkyl di-nitro dehydro-abietate 11 to alkyl di-amino dehydro-abietate 12, and (iv) phosgenation of the alkyl di-amino dehydro-abietate 12 to the biobased alkyl di-isocyanato dehydro-abietate 2 (FIG. 3).

A process for the preparation of the biobased diisocyanate of formula 3, may comprise the steps of: (i) esterification of dehydro-abietic acid 9 to bis-(dehydro-abietate) alkane 13, (ii) nitration of the bis-(dehydro-abietate) alkane 13 to bis-(nitro-dehydro-abietate) alkane 14, (iii) reduction of the bis-(nitro-dehydro-abietate) alkane 14 to bis-(amino-dehydro-abietate) alkane 15, and (iv) phosgenation of the bis-(amino-dehydro-abietate) alkane 15 to the bis-(isocyanato-dehydro-abietate) alkane 3 (FIG. 4).

Also contemplated is a polyurethane elastomer derived from the biobased diisocyanate and a polyester resin. The polyester resin may be a biobased polyester resin.

Accordingly, in one aspect there is provided a biobased diisocyanate of the formula 1, 2 or 3 (FIG. 1), where: R is an alkylene of from about 2 to about 12 carbon atoms, and R' is an alkyl group of from about 1 to about 12 carbon atoms.

Formula 1 may be 8, 11-diisocyanato-2-isopropyl-4b, 8-dimethyl-4, 4a, 4b, 5,6,7, 8, 8a, 9, 10-decahydro-3H-3, 10a-ethanophenanthrene.

Formula 2 may be selected from the group consisting of: methyl 12,14-di-nitro-dehydroabietate, ethyl 12, 14-di-nitro-dehydroabietate, propyl 12, 14-di-nitro-dehydroabietate, butyl 12, 14-di-nitro-dehydroabietate, pentyl 12, 14-di-nitro-dehydroabietate, hexyl 12, 14-di-nitro-dehydroabietate, heptyl 12, 14-di-nitro-dehydroabietate, octyl 12, 14-di-nitro-dehydroabietate, nonyl 12, 14-di-nitro-dehydroabietate, decyl 12, 14-di-nitro-dehydroabietate, undecyl 12, 14-di-nitro-dehydroabietate, dodecyl 12,14-di-nitro-dehydroabietate, and mixtures thereof.

Formula 3 may be selected from the group consisting of: bis-(12-isocyanato-dehydroabiete) ethane, 1-(12-isocyanato-dehydroabietate)-n'-(14-isocyanato-dehydroabietate) ethane, bis-(14-isocyanato-dehydroabiete) ethane, bis-(12-isocyanato-dehydroabiete) propane, 1-(12-isocyanato-dehydroabietate)-n'-(14-isocyanato-dehydroabietate) propane, bis-(14-isocyanato-dehydroabiete) propane, bis-(12-isocyanato-dehydroabiete) butane, 1-(12-isocyanato-dehydroabietate)-n'-(14-isocyanato-dehydroabietate) butane, bis-(14-isocyanato-dehydroabiete) butane, bis-(12-isocyanato-dehydroabiete) hexane, 1-(12-isocyanato-dehydroabietate)-n'-(14-isocyanato-dehydroabietate) hexane, bis-(14-isocyanato-dehydroabiete) hexane, bis-(12-isocyanato-dehydroabiete) octane, 1-(12-isocyanato-dehydroabietate)-n'-(14-isocyanato-dehydroabietate) octane, bis-(14-isocyanato-dehydroabiete) octane, and mixtures thereof.

The biobased diisocyanate may be from about 70% to about 95% biobased, by total weight of the diisocyanate.

A process for the preparation of the biobased diisocyanate of formula 1, may comprise the steps of: (i) alkylation or esterification of rosin diacid or acrylic pimaric acid to rosin diester (ii) conversion of the rosin diester to rosin di-hydrazide, (iii) azidation of the rosin di-hydrazide to rosin di-azide, and (iv) subsequent heating to rosin diisocyanate.

A process for the preparation of the biobased diisocyanate of formula 1, may comprise the steps of: (i) anhydridification of rosin diacid or acrylic pimaric acid to rosin di-(ethyl carbonic) anhydride, (ii) conversion of the rosin di-(ethyl carbonic) anhydride to rosin di-azide, and (iii) subsequent heating to rosin diisocyanate.

A process for the preparation of the biobased diisocyanate of formula 2, may comprise the steps of: (i) esterification of dehydro-abietic acid to alkyl dehydro-abietate, (ii) di-nitration of the alkyl dehydro-abietate to alkyl di-nitro dehydro-abietate, (iii) reduction of the alkyl di-nitro dehydro-abietate to alkyl di-amino dehydro-abietate, and (iv) phosgenation of the alkyl di-amino dehydro-abietate to alkyl di-isocyanato dehydro-abietate.

A process for the preparation of the biobased diisocyanate of formula 3, may comprise the steps of: (i) esterification of dehydro-abietic acid to bis-(dehydro-abietate) alkane, (ii) nitration of the bis-(dehydro-abietate) alkane to bis-(nitro-dehydro-abietate) alkane, (iii) reduction of the bis-(nitro-dehydro-abietate) alkane to bis-(amino-dehydro-abietate) alkane, and (iv) phosgenation of the bis-(amino-dehydro-abietate) alkane to bis-(isocyanato-dehydro-abietate) alkane.

In one embodiment, there is provided a polyurethane elastomer derived from: any of the biobased diisocyanates described in this aspect; and a polyester resin.

From about 85% to about 99% of the weight of the polyurethane elastomer may be derived from biobased content.

The polyurethane elastomer may further comprise one or more of a plasticizer, a colorant, a foaming agent, a chain extender, a bio-additive, and a polymerization catalyst.

BRIEF DESCRIPTION OF THE DRAWINGS

Embodiments will now be described more fully with reference to the accompanying drawings in which.

DETAILED DESCRIPTION OF THE INVENTION

Figure 1:
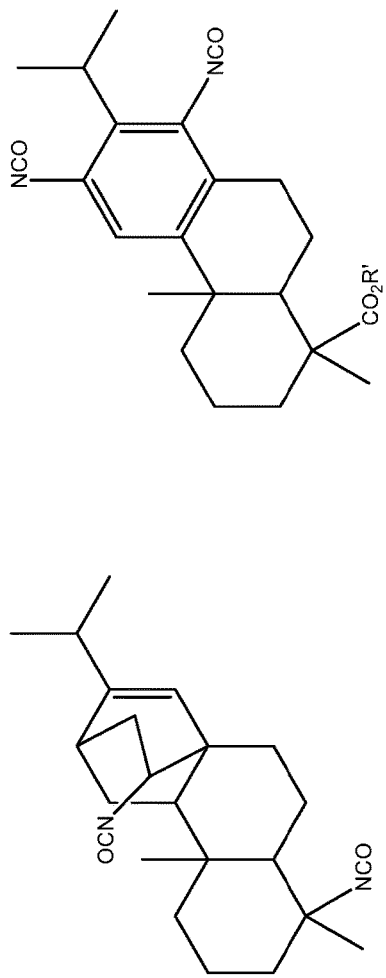
FIG. 1 is a structural view of biobased diisocyanates.
Figure 1:
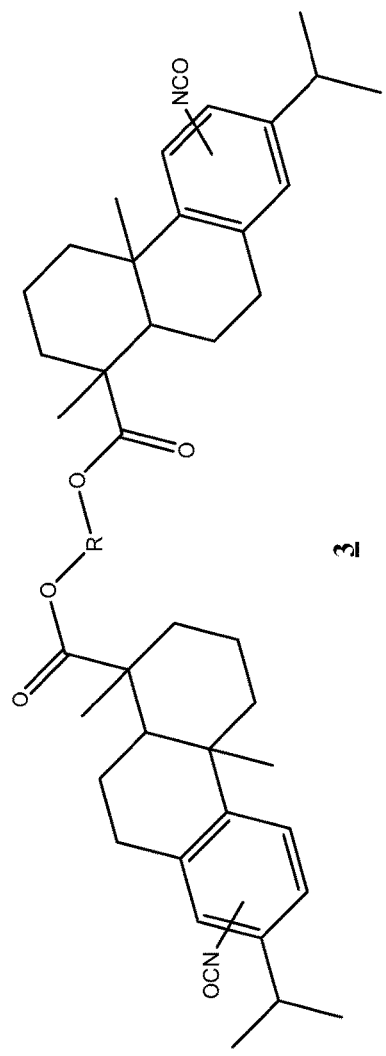
Figure 1:
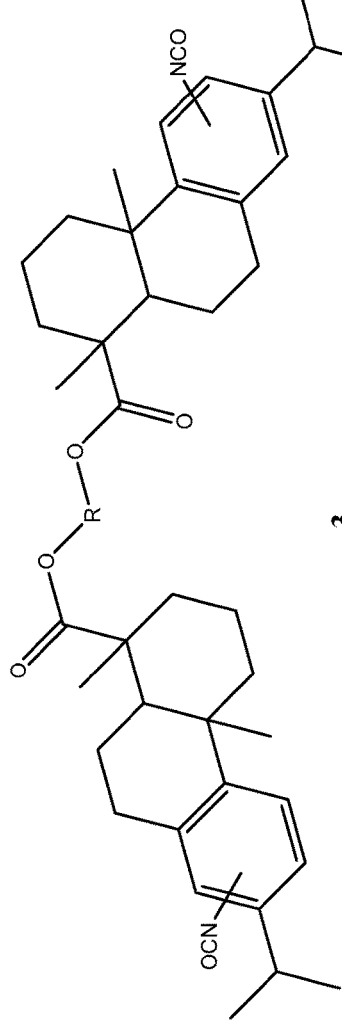

FIG. 1 shows biobased diisocyanates of formulas 1, 2 and 3, where R is an alkylene of from about 2 to about 12 carbon atoms, and where R' is an alkyl group of from about 1 to about 12 carbon atom such as methyl, ethyl, propyl, butyl, etc.

The biobased diisocyanate of formula 1 is a rosin diisocyanate and can be named in accordance with IUPAC nomenclature as 8,11-diisocyanato-2-isopropyl-4b,8-dimethyl-4,4a,4b,5,6,7,8,8a,9,10-decahydro-3H-3,10a-ethanophenanthrene.

The biobased diisocyanate of formula 2, is selected from the group consisting of alkyl 12,14-diisocyanato dehydroabietate, wherein the alkyl group R' is any of methyl, ethyl, propyl, butyl, pentyl, hexyl, heptyl, octyl, nonyl, decyl, undecyl and dodecyl.

The biobased diisocyanate of formula 3 is selected from the group consisting of bis (isocyanato-dehydro-abietate) alkane.

The biobased diisocyanate 1 of the present invention may be prepared utilizing three distinct process steps starting from rosin diacid 4 (acrylic pimaric acid), whereby the steps are common to established procedures in the art such as those described by Hai et al., in "Preparation of Mono- and Diisocyanates in Flow from Renewable Carboxylic Acids", Org. Process Res. Dev., Vol 24, p. 2342-2346 (2020), or such as those described in Organic Syntheses, Coll. Vol. 6, p. 910 (1988); Vol. 51, p. 48 (1971).

The biobased diisocyanates 2 and 3 of the present invention may be prepared utilizing four distinct process steps starting from dehydro-abietic acid 9, whereby three of the steps are common to established procedures in the art of preparing traditional fossil fuel aromatic based diisocyanates such as toluene diisocyanate (TDI). These three common steps are nitration, reduction (hydrogenation) and phosgenation. In the present invention, an additional process step is performed to protect the carboxylic acid group of dehydro-abietic acid 9, by either an esterification or alkylation process, to yield the alkyl dehydro-abietate 10 (FIG. 3); or by the esterification of dehydro-abietic acid 9 to the bis-(dehydro-abietate)-alkane 13 (FIG. 4).

Figure 5:
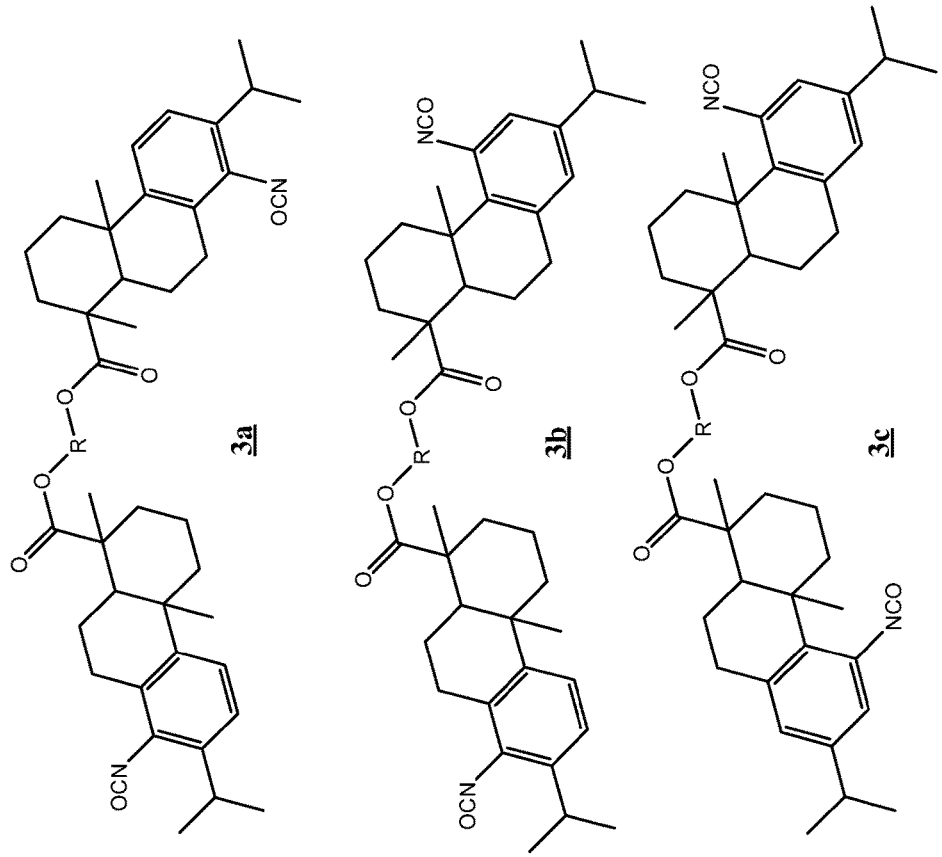
FIG. 5 is a structural view of isomers of the biobased diisocyanate 3 of FIG. 1.

FIG. 5 shows exemplary embodiments of the biobased diisocyanate 3 illustrated in FIG. 1. These can be defined as bis-(12-isocyanato-dehydroabiete) alkane (3a), 1-(12-isocyanato-dehydroabietate)-n'-(14-isocyanato-dehydroabietate)-alkane (3b), and bis-(14-isocyanato-dehydroabiete) alkane (3c), and mixtures thereof are contemplated.

Figure 2:
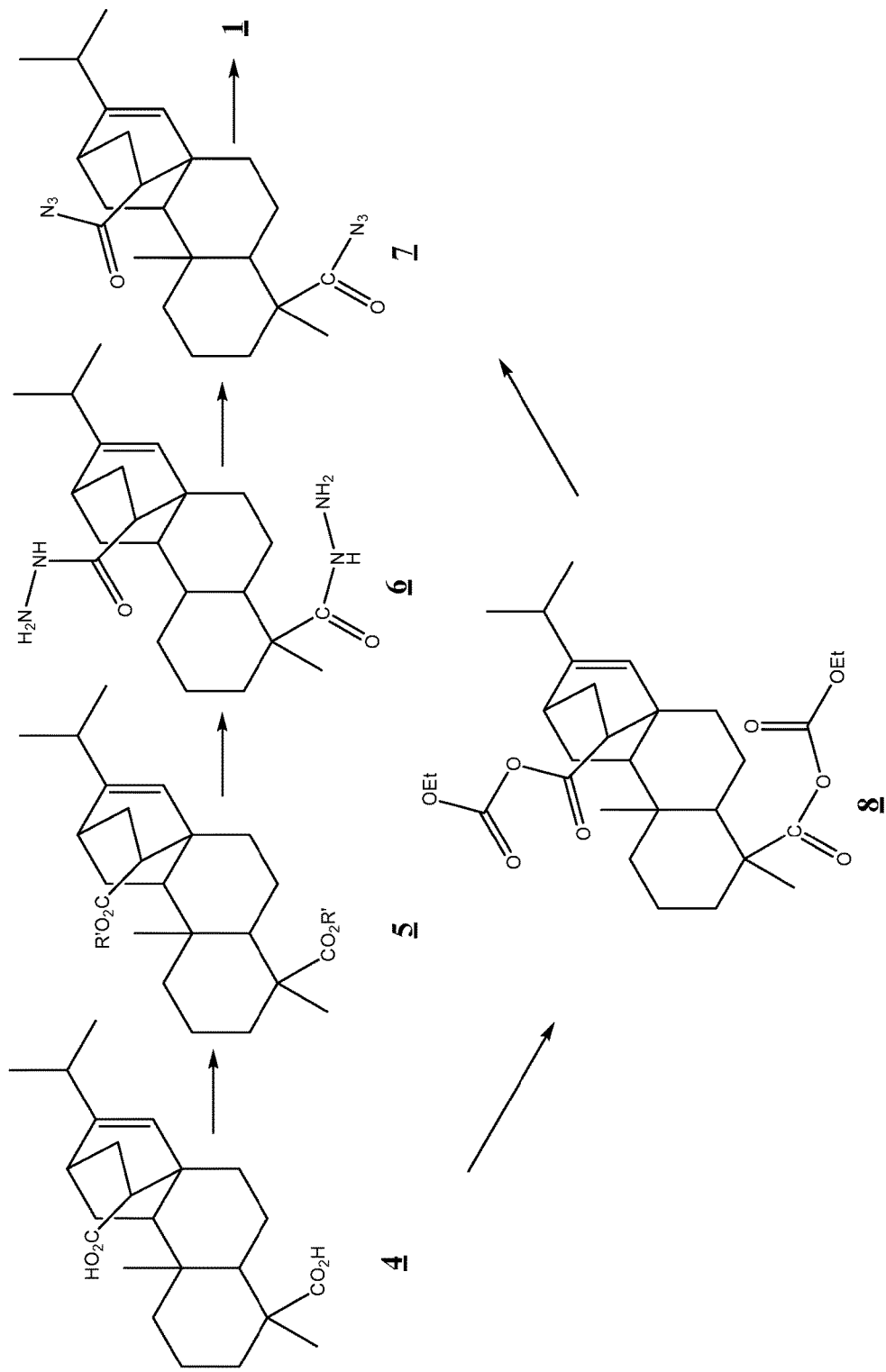
FIG. 2 is a view of process steps used for synthesis of the biobased diisocyanate 1 of FIG. 1.

The preferred process for the synthesis of the biobased diisocyanate 1 illustrated in FIG. 1, is shown in FIG. 2 and comprises the steps of: (i) alkylation or esterification of rosin diacid 4 to rosin diester 5 (ii) conversion of the rosin diester 5 to rosin di-hydrazide 6, (iii) followed by preparation of rosin di-azide 7 from the rosin di-hydrazide 6, with subsequent heating via the Curtius rearrangement to the rosin diisocyanate 1. Alternatively, the process may comprise the steps of (i) anhydridification of rosin diacid 4 to rosin di-(ethyl carbonic) anhydride 8 (ii) and conversion of the rosin di-(ethyl carbonic) anhydride 8 to rosin di-azide 7, with subsequent heating via the Curtius rearrangement to the rosin diisocyanate 1 (FIG. 2).

Figure 3:
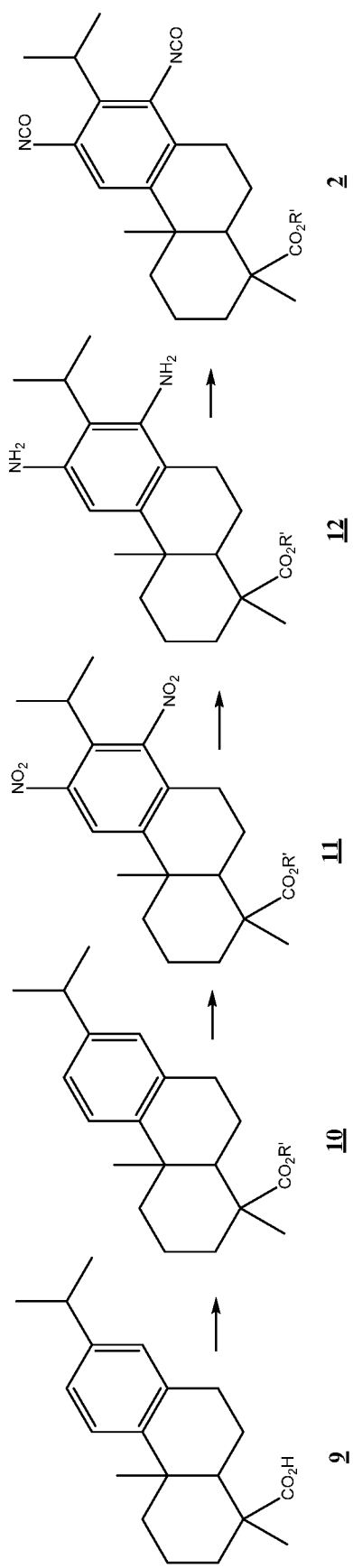
FIG. 3 is a view of process steps used for synthesis of the biobased diisocyanate 2 of FIG. 1.
Figure 4:
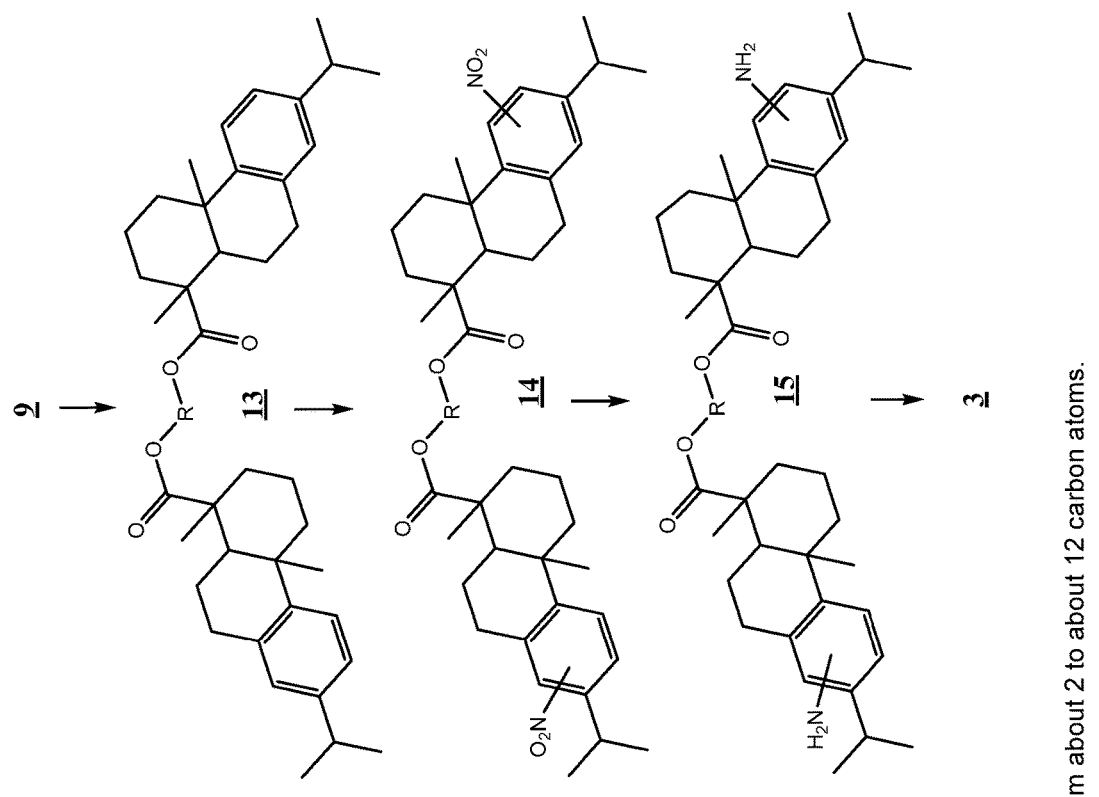
FIG. 4 is a view of process steps used for synthesis of the biobased diisocyanate 3 of FIG. 1.

The preferred process for the preparation of the biobased diisocyanate 2 illustrated in FIG. 1, wherein R' is an alkyl group from about 1 to about 12 carbon atoms, such as methyl, ethyl, propyl, butyl, hexyl, heptyl, octyl, etc., is shown in FIG. 3 and comprises the steps of: (i) esterification of dehydro-abietic acid 9 to alkyl dehydro-abietate 10, (ii) di-nitration of the alkyl dehydro-abietate 10 to alkyl di-nitro dehydro-abietate 11, (iii) reduction of the alkyl di-nitro dehydro-abietate 11 to alkyl di-amino dehydro-abietate 12, and (iv) phosgenation of the alkyl di-amino dehydro-abietate 12 to the biobased alkyl di-isocyanato dehydro-abietate 2 (FIG. 3).

The preferred process for the preparation of the biobased diisocyanate 3 illustrated in FIG. 1, wherein R is an alkylene from about 2 to about 12 carbon atoms such as ethylene, propylene, butylene, pentylene, hexylene, etc., is shown in FIG. 4 and comprises the steps of: (i) esterification of dehydro-abietic acid 9 to bis-(dehydro-abietate) alkane 13, (ii) nitration of the bis-(dehydro-abietate) alkane 13 to bis-(nitro-dehydro-abietate) alkane 14, (iii) reduction of the bis-(nitro-dehydro-abietate) alkane 14 to bis-(amino-dehydro-abietate) alkane 15, and (iv) phosgenation of the bis-(amino-dehydro-abietate) alkane 15 to the bis-(isocyanato-dehydro-abietate) alkane 3 (FIG. 4).

Alkylation/Esterification

The alkylation or esterification of rosin diacid 4 to rosin diester 5, or of dehydro-abietic acid 9 to alkyl dehydroabietate 10 can be achieved by well-known methods such as the Fisher esterification whereby the organic carboxylic acid is heated with an alcohol in the presence of an acid catalyst, generating water as a byproduct. The esterification of rosin diacid 4 to rosin diester 5 can be accomplished utilizing methyl iodide, methyl sulfate or dimethyl carbonate, as described by Selva and Perosa, in "Green chemistry metrics: a comparative evaluation of dimethyl carbonate, methyl iodide, dimethyl sulfate and methanol as methylating agents", Green Chemistry 10, p. 457 (2008).

The esterification of dehydro-abietic acid 9 to bis-(dehydro-abietate) alkane 13, can be accomplished by known methods such as heating an organic acid such as 9 with an alkylene glycol such as ethylene glycol, propylene glycol, butylene glycol, pentylene glycol, hexylene glycol or octylene glycol, in the presence of a catalyst and generating water as the by-product.

Rosin Di-Hydrazide and Di-Azide Formation

The conversion of rosin diester 5 to rosin di-hydrazide 6, can be accomplished by heating an ester with hydrazine and generating alcohol as a by-product, followed by adding sodium nitrate and hydrochloric acid to obtain rosin di-azide 7, utilizing a general procedure described by Hai et al., Org. Process Res. Dev., Vol 24, p. 2342-2346 (2020).

Anhydridification and Di-Azide Formation

The anhydridification of rosin diacid 4 to rosin di-(ethyl carbonic) anhydride 8, and conversion of the rosin di-(ethyl carbonic) anhydride 8 to rosin di-azide 7, can be achieved in a one pot reaction, whereby an organic carboxylic acid is reacted with ethyl chloro-carbonate and triethyl amine, followed by adding sodium azide in water, as described in Organic Syntheses, Coll. Vol. 6, p. 910 (1988); Vol. 51, p. 48 (1971).

Curtius Rearrangement

The Curtius rearrangement of rosin diazide 7 to rosin diisocyanate 1 is accomplished by heating in a solvent such as toluene, or alternatively by heating at low temperature in the presence of a Lewis acid and generating nitrogen as a by-product, as described by Zabalov et al., Journal of Molecular Structure: THEOCHEM 962, 15-22 (2010).

Nitration

The di-nitration of alkyl dehydro-abietate 10 to alkyl di-nitro dehydro-abietate 11 can be achieved utilizing nitric acid in the presence of sulfuric acid, as described in U.S. Pat. No. 2,803,645.

The di-nitration of bis-(dehydro-abietate) alkane 13 to bis-(nitro-dehydro-abietate) alkane 14 can also be achieved utilizing nitric acid in the presence of acetic anhydride, as described by Levinson, J. Org. Chem., Vol. 86, No. 20, 1971. Other organic solvents suitable for these transformations, such as dichloromethane, ether, tetrahydrofuran, can be utilized by those skilled in the art. The nitric acid can be utilized in a concentration of 50% to about 90%, or fuming nitric acid may alternatively be used. Acetic acid, acetic anhydride and sulfuric acid can also be utilized in combination with the nitric acid. The various nitration products can be isolated by aqueous (basic) extraction of the residual acid, followed by solvent evaporation, and optionally recrystallization of the products. Other known methods of nitration of aromatic compounds are known, such as the solventless process described by Hajipour and Ruoho, in "A Fast and Mild Method for Nitration of Aromatic Ring", Phosphorus, Sulfur, and Silicon, 179, p. 221-226 (2004), whereby benzyltriphenylphosphonium nitrate and methanesulfonic acid are utilized with aromatic phenols and anisoles to obtain high yields of nitrated aromatic compounds without the use of solvents. Other known methods of nitration practiced industrially for production of di-nitrotoluene used in the production of TDI can be used, such as those disclosed in U.S. Pat. No. 9,428,441, and in prior art documents cited therein.

Reduction (Hydrogenation)

The reduction of di-nitro aromatic compounds 11 and 14, to di-amino aromatic compounds 12 and 15, respectively, can be preferably accomplished by hydrogenation with a catalyst with hydrogen under pressure, as described in U.S. Pat. Nos. 3,328,465, 3,356,728 and 3,517,063, wherein the aromatic dinitro compound is dissolved in a solvent such as methanol and a catalyst such as Raney nickel is employed, at a temperature of from about 100° C. to about 150° C. under a hydrogen pressure of from about 50 atmosphere to about 250 atmosphere. Other catalysts such as platinum, palladium or a combination of platinum and palladium deposited on a carbon support which may be porous or non-porous, can also be utilized. Other methods of reduction of nitro aromatics to amino aromatics are known, such as chemo selective mild reduction described by Kumar et al., in "Simple and chemoselective reduction of aromatic nitro compounds to aromatic amines: reduction with hydriodic acid revisited", Tetrahedron Letters 42, p. 5601 (2001), wherein hydroiodic acid is utilized at about 90° C. for 2 to 4 hours to reduce the nitro aromatic compounds to amino aromatic compounds in high yield. Additional methods such as those described by Lauwiner et al., in Applied Catalysis A: General 177, p. 9 (1999), can be utilized in the reduction of aromatic nitro compounds with hydrazine hydrate in the presence of an iron oxide/hydroxide catalyst. Other catalysts with hydrazine such as ruthenium have also been reported for the reduction of aromatic nitro compounds. The present invention is not limited to the above reduction process(es), and a variety of processes known in the literature can alternatively be utilized by those skilled in the art.

Phosgenation

The diamino aromatic compounds 12 and 15 can be transformed into biobased aromatic diisocyanates 2 and 3 respectively, utilizing phosgene gas, and similarly to the production process of toluene diisocyanate described in U.S. Pat. No. 8,034,972, and in prior art documents cited therein. Other known methods utilizing diphosgene (trichloromethyl chloroformate) or triphosgene also known as bis(trichloromethyl) carbonate, which is in liquid rather than gaseous form, can be utilized for the preparation or aromatic diisocyanates from aromatic diamines. A variety of solvents can be utilized for this process, including aprotic solvents such as alkanes, dichloromethane, ether, tetrahydrofuran, ethyl acetate, acetonitrile, and the like, at a temperature range of from about 0° C. to about 60° C., followed by solvent removal by distillation. The resulting diisocyanate products can be optionally fractionally distilled under reduced pressure, recrystallized, or utilized without purification.

The present invention also contemplates a polyurethane elastomer derived primarily from a two-component reaction or curing of the biobased diisocyanate of formula 1, 2 or 3, and a polyol. Preferably, the polyol is a biobased polyol. In ideal circumstances, the polyol is in liquid form during the reaction at a temperature from about 25° C. to about 80° C. Polyols derived from ethylene oxide and or propylene oxide are typically liquid and of low viscosity under these conditions, although these polyols are generally derived from fossil fuels. Polyols comprised of polyester resins with hydroxyl terminated end groups may also be used, and in some instances are derived from biomass or biobased materials such as those disclosed in U.S. Pat. No. 10,934,384 to Evoco Ltd., issued Mar. 2, 2021, the content of which is incorporated herein by reference in its entirety. These polyester polyols can be solid or viscous liquids at the temperature range of from about 25° C. to about 80° C., and thus require the use of diluents to render them to liquid states. Since there is a desire to utilize biobased polyester polyols, biobased plasticizers can be utilized as effective diluents to solubilize the polyester polyol to a liquid of low viscosity for providing the plasticization of the resulting polyurethane elastomer. Ideally, the amount of plasticizer should be added in a minimal enough quantity to solubilize the polyester polyol, and to provide a desirable level of plasticization of the resulting polyurethane elastomer. Such biobased plasticizers have been described, for example, in co-pending U.S.

application Ser. No. 17/176,874 to Evoco Ltd., filed Feb. 16, 2021, the content of which is incorporated herein by reference in its entirety. From about 85 to about 99% of the weight of the polyurethane elastomer may be derived from biobased content.

Specific embodiments of the present disclosure as illustrated in the following Examples are for illustrative purposes, and are not limited to the materials, conditions, or process parameters set forth therein.

Example 1

Preparation of Rosin Diacid (4).

To a 500 ml three-necked flask equipped with a magnetic stirrer, a reflux condenser and a thermometer, was added 100 grams of gum rosin (obtained from Boluo Changning Yuandongxing Chemical Co., China) To this was added 25 g of acrylic acid and 0.5 g of hydroquinone (polymerization inhibitor), and this mixture was stirred under nitrogen to 200° C. over 3 hours and maintained at 200° C. for an additional 5 hours. The reaction was then cooled to room temperature and then dissolved in 100 grams of ethyl ether, followed by precipitating the product with 700 mL of heptane. The precipitate was filtered to obtain 55 grams of rosin diacid 4, which was characterized by nuclear magnetic resonance (NMR) spectroscopy.

Example 2

Preparation of Rosin Di-azide (7).

To a 100 ml three-necked flask equipped with a magnetic stirrer, a reflux condenser, and a thermometer, was added 25 grams of the rosin diacid 4 of Example 1 and 100 grams of dry acetone. The flask was cooled in an ice-water bath to about 0 to 5° C. To this was added 15.9 grams of ethyl chloroformate, followed by dropwise addition of 14.8 grams of triethyl amine for 10 minutes. The mixture was stirred for an additional hour to obtain rosin di-(ethyl carbonic) anhydride 8 which was not isolated, followed by the addition of 17 grams of sodium azide in 50 mL of water over a 20-minute period. The mixture was allowed to warm up to room temperature over a 1-hour period, and was then poured into a 1 L beaker containing 500 mL of ice-water. That mixture was allowed to warm to room temperature over a 2-hour period, and the product was then extracted with ether (2×100 mL). The organic extract was then washed with water, dried over sodium sulfate and rotary evaporated at reduced pressure at 30° C., to yield the rosin di-azide 7 as a paste, which was characterized by NMR spectroscopy.

Example 4

Preparation of Rosin Di-ester (5) (R'=CH$_3$).

To a 300 ml Parr reactor equipped with a stirrer, a reflux condenser, and a receiver was added 50 grams of the rosin di-acid 4 of Example 1, 100 grams of dimethyl carbonate, 0.5 grams of potassium carbonate and 0.1 g of tetraethyl-ammonium bromide. The mixture was heated to 160° C. over a 1-hour period and maintained at 160° C. for 12 hours under pressure. The mixture was then allowed to cool to room temperature, dissolved in ethyl acetate, washed with water, and dried over sodium sulfate, and the solvent was then removed under reduced pressure with a rotary-evaporator to yield the rosin di-methyl ester 5 (R'=CH$_3$).

Example 5

Preparation of Rosin Di-hydrazide (6).

To a 300 ml 3-necked flask equipped with a magnetic stirrer and a reflux condenser was added 25 grams of the rosin di-ester 5 of Example 4 and 6 grams of hydrazine hydrate (80%). The mixture was heated under nitrogen to 60° C. for 1.5 hours and then poured into a 250 ml beaker containing 100 grams of water, and filtered to yield the rosin di-hydrazide 6.

Example 6

Preparation of Rosin Di-azide (7).

To a 100 ml three-necked flask equipped with a magnetic stirrer and a thermometer was added 25 grams of the rosin di-hydrazide 6 of Example 5 and 50 grams of ethyl ether, and the flask was cooled in an ice-water bath to between about 0° C. and about 5° C. To this was added a solution of 5 grams of sodium nitrite in 20 mL of water, followed by dropwise addition of 3 mL of a 1 M HCl aqueous solution. The mixture was stirred for 15 minutes, and the organic layer was separated, dried with sodium and rotary-evaporated under reduced pressure at 30° C., to yield the rosin di-azide 7.

Example 7

Preparation of Rosin Diisocyanate (1).

To a 100 ml three-necked flask equipped with a magnetic stirrer, a reflux condenser, and a thermometer was added 25 grams of the rosin di-azide 7 of Example 2 or Example 6, and 100 grams of dry toluene. The mixture was heated under nitrogen slowly to 60° C. over a 1-hour period, followed by heating to 80° C. over a 1-hour period, and was then maintained at 80° C. for an additional 2 hours. The mixture was then allowed to cool to room temperature, and the solvent was removed under reduced pressure with a rotary-evaporator to yield the rosin diisocyanate 1.

Example 8

Preparation of Methyl Dehydro-abietate (10) (R'=CH$_3$).

To a 300 ml Parr reactor equipped with a stirrer, a reflux condenser, and a receiver was added 50 grams of dehydro-abietic acid 9, 50 grams of dimethyl carbonate, 0.5 grams of potassium carbonate and 0.1 g of tetraethyl-ammonium bromide. The mixture was heated to 160° C. over a 1-hour period and maintained at 160° C. for 12 hours under pressure. The mixture was then allowed to cool to room temperature, dissolved in ethyl acetate, washed with water, and dried over sodium sulfate, and the solvent was then removed under reduced pressure with a rotary-evaporator to yield the methyl dehydro-abietate 10 (R'=CH$_3$).

Example 9

Preparation of Methyl 12,14-dinitro Dehydro-abietate (11) (R'=CH$_3$).

To a 300 mL volumetric flask equipped with a magnetic stirrer was added 50 mL of concentrated sulfuric acid 25 mL of 90% nitric acid. The volumetric flask was cooled in an ice-water bath to between about 0° C. and about 5° C. To this was then slowly added 20 grams of the methyl dehydro-abietate 10 of Example 8 over a 10-minute period. The mixture was kept at about 0° C. to about 5° C. for 1 hour, and was then allowed to warm up to room temperature overnight. The mixture was then poured into ice water, and the precipitate was filtered off to yield the methyl 12,14-dinitro dehydro-abietate 11 (R'=CH$_3$).

Example 10

Preparation of Methyl 12,14-di-amino Dehydro-abietate (12) (R'=CH$_3$).

A mixture of 18 grams of the methyl 12,14-dinitro dehydro-abietate 11 of Example 9, 50 ml of absolute ethanol, and 0.25 g of Raney nickel was placed in a steel reaction vessel (or "bomb") of a high-pressure hydrogenation apparatus. The bomb was then closed, and hydrogen was admitted until the pressure, at 25° C., was about 1000 psi. While the bomb was shaken, the temperature was rapidly raised to between 80° C. and 90° C., and the heater was then shut off. The pressure in the reaction vessel was maintained at between 700 psi and 1500 psi by introducing hydrogen from a tank, until the rapid reaction was over (about 15 minutes). The reaction mixture was kept between 100° C. and 120° C. for 30 minutes after there was no further drop in the pressure of hydrogen. After the bomb had cooled, the hydrogen was slowly released and the catalyst was separated from the reaction mixture by centrifuging. The product was then collected by filtration to yield the methyl 12,14-di-amino dehydro-abietate 12 (R'=CH$_3$).

Example 11

Preparation of Methyl 12,14-di-isocyanato Dehydro-abietate (2) (R'=CH$_3$).

To a 250 mL 3 necked flask equipped with a magnetic stirrer and reflux condenser was added 100 mL of ethyl acetate, 15 grams of the 12,14-di-amino dehydro-abietate 12 (R'=CH$_3$) of Example 11, and a solution of 12 g triphosgene in 50 mL of ethyl acetate over a 20-minute period. The mixture was then refluxed under nitrogen for 4 hours. After allowing the reaction to cool to room temperature, the solvent was evaporated under reduced pressure and the residue obtained was subjected to distillation in a Kugelrohr apparatus, to yield 15.5 grams of the methyl 12,14-di-isocyanato dehydro-abietate 2.

Example 12

Preparation of Bis-(dehydro-abietate) Propane (13) (R=CH$_2$CH$_2$CH$_2$).

To a 300 ml 3-necked flask equipped with a magnetic stirrer and a reflux condenser and receiver, was added 30 grams of dehydro-abietic acid 9, 10 grams of 1,3-propane-diol and 0.21 grams of titanium (IV) isopropoxide. The mixture was heated to 190° C. over a 2-hour period under nitrogen, and then maintained at 190° C. for an additional two hours. The mixture was then heated to 210° C., and the pressure was reduced from atmospheric pressure to 10 mm-Hg over a 1-hour period during which water and excess 1,3-propane-diol was collected. The mixture was then maintained for an additional hour, after which the pressure was returned to atmospheric with nitrogen. The product was allowed to cool to room temperature to yield the bis-(dehydro-abietate) propane 13 (R=CH$_2$CH$_2$CH$_2$).

Example 13

Preparation of Bis-(nitro-dehydro-abietate) Propane (14) (R=CH$_2$CH$_2$CH$_2$).

To a 300 mL volumetric flask equipped with a magnetic stirrer was added 30 grams of the bis-(dehydro-abietate) propane 13 of Example 12 and 150 mL of acetic anhydride. The mixture was stirred at 25° C., and to this was added dropwise a solution of 6.6 grams of 90% nitric acid in 10 grams of acetic anhydride over a 30-minute period. The volumetric flask was stirred for an additional 2 hours, after which the mixture was poured into a 500 mL beaker containing 250 grams of ice-water. The mixture then allowed to warm up to room temperature over a 2-hour period, and the precipitate was filtered off to yield the bis-(nitro-dehydro-abietate) propane 14.

Example 14

Preparation of Bis-(amino-dehydro-abietate) Propane (15) (R=CH$_2$CH$_2$CH$_2$).

A mixture of 20 grams of the bis-(nitro-dehydro-abietate) propane 14 of Example 13, 50 mL of absolute ethanol, and 0.25 grams of Raney nickel was placed in a steel reaction vessel (or "bomb") of a high-pressure hydrogenation apparatus. The bomb was then closed, and hydrogen was admitted until the pressure, at 25° C., was about 1000 psi. While the bomb was shaken, the temperature was rapidly raised to between 80° C. and 90° C., and the heater was then shut off. The pressure in the reaction vessel was maintained at between 700 psi and 1500 psi by introducing hydrogen from a tank, until the rapid reaction was over (about 15 minutes). The reaction mixture was kept between 100° C. and 120° C. for 30 minutes after there was no further drop in hydrogen pressure. After the bomb had cooled, the hydrogen was slowly released, and the catalyst was separated from the reaction mixture by centrifuging. The product was collected by filtration to yield the bis-(amino-dehydro-abietate) propane 15.

Example 15

Preparation of Bis-(isocyanato-dehydro-abietate) Propane (3) (R=CH$_2$CH$_2$CH$_2$).

To a 250 mL 3-necked flask equipped with a magnetic stirrer and reflux condenser was added 100 mL of ethyl acetate, 15 grams of the bis-(amino-dehydro-abietate) propane 15 of Example 14, and a solution of 6.2 g triphosgene in 50 mL of ethyl acetate over a 20-minute period. The mixture was then refluxed under nitrogen for 4 hours. After allowing the reaction to cool to room temperature, the solvent was evaporated under reduced pressure and the residue obtained was subjected to distillation in a Kugelrohr apparatus, to yield the methyl 12,14-di-isocyanato dehydro-abietate 3.

What is claimed is:
1. A biobased diisocyanate of the formula 1 or 3:

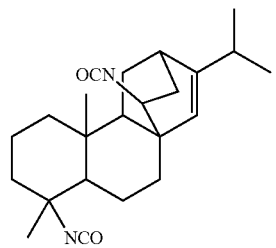

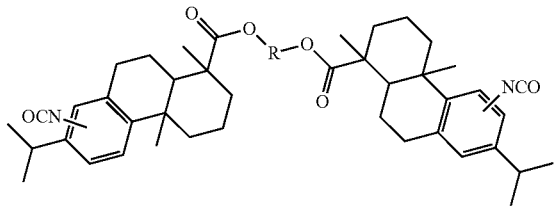

where:

R is an alkylene of from about 2 to about 12 carbon atoms.

2. The biobased diisocyanate of claim 1, wherein formula 1 is 8,11-diisocyanato-2-isopropyl-4b,8-dimethyl-4,4a,4b,5,6,7,8,8a,9,10-decahydro-3H-3,10a-ethanophenanthrene.

3. The biobased diisocyanate of claim 1, wherein formula 3 is selected from the group consisting of: bis-(12-isocyanato-dehydroabiete) ethane, 1-(12-isocyanato-dehydroabietate)-n'-(14-isocyanato-dehydroabietate) ethane, bis-(14-isocyanato-dehydroabiete) ethane, bis-(12-isocyanato-dehydroabiete) propane, 1-(12-isocyanato-dehydroabietate)-n'-(14-isocyanato-dehydroabietate) propane, bis-(14-isocyanato-dehydroabiete) propane, bis-(12-isocyanato-dehydroabiete) butane, 1-(12-isocyanato-dehydroabietate)-n'-(14-isocyanato-dehydroabietate) butane, bis-(14-isocyanato-dehydroabiete) butane, bis-(12-isocyanato-dehydroabiete) hexane, 1-(12-isocyanato-dehydroabietate)-n'-(14-isocyanato-dehydroabietate) hexane, bis-(14-isocyanato-dehydroabiete) hexane, bis-(12-isocyanato-dehydroabiete) octane, 1-(12-isocyanato-dehydroabietate)-n'-(14-isocyanato-dehydroabietate) octane, bis-(14-isocyanato-dehydroabiete) octane, and mixtures thereof.

4. The biobased diisocyanate of claim 1, wherein the diisocyanate is from about 70% to about 95% biobased, by total weight of the diisocyanate.

5. A process for the preparation of the biobased diisocyanate of claim 1, formula 1, comprising the steps of: (i) alkylation or esterification of rosin diacid or acrylic pimaric acid to rosin diester (ii) conversion of the rosin diester to rosin di-hydrazide, (iii) azidation of the rosin di-hydrazide to rosin di-azide, and (iv) subsequent heating to rosin diisocyanate.

6. A process for the preparation of the biobased diisocyanate of claim 1, formula 1, comprising the steps of: (i) anhydridification of rosin diacid or acrylic pimaric acid to rosin di-(ethyl carbonic) anhydride, (ii) conversion of the rosin di-(ethyl carbonic) anhydride to rosin di-azide, and (iii) subsequent heating to rosin diisocyanate.

7. A process for the preparation of the biobased diisocyanate of claim 1, formula 3, comprising the steps of: (i) esterification of dehydro-abietic acid to bis-(dehydro-abietate) alkane, (ii) nitration of the bis-(dehydro-abietate) alkane to bis-(nitro-dehydro-abietate) alkane, (iii) reduction of the bis-(nitro-dehydro-abietate) alkane to bis-(amino-dehydro-abietate) alkane, and (iv) phosgenation of the bis-(amino-dehydro-abietate) alkane to bis-(isocyanato-dehydro-abietate) alkane.

8. A polyurethane elastomer derived from:
the biobased diisocyanate of claim 1; and
a polyester resin.

9. The polyurethane elastomer of claim 8, wherein the biobased diisocyanate is the biobased diisocyanate of formula 1, and is 8,11-diisocyanato-2-isopropyl-4b,8-dimethyl-4,4a,4b,5,6,7,8,8a,9,10-decahydro-3H-3,10a-ethanophenanthrene.

10. The polyurethane elastomer of claim 8, wherein the biobased diisocyanate is the biobased diisocyanate of formula 3, and is selected from the group consisting of: bis-(12-isocyanato-dehydroabiete) ethane, 1-(12-isocyanato-dehydroabietate)-n'-(14-isocyanato-dehydroabietate) ethane, bis-(14-isocyanato-dehydroabiete) ethane, bis-(12-isocyanato-dehydroabiete) propane, 1-(12-isocyanato-dehydroabietate)-n'-(14-isocyanato-dehydroabietate) propane, bis-(14-isocyanato-dehydroabiete) propane, bis-(12-isocyanato-dehydroabiete) butane, 1-(12-isocyanato-dehydroabietate)-n'-(14-isocyanato-dehydroabietate) butane, bi s-(14-isocyanato-dehydroabiete) butane, bi s-(12-isocyanato-dehydroabiete) hexane, 1-(12-isocyanato-dehydroabietate)-n'-(14-isocyanato-dehydroabietate) hexane, bi s-(14-isocyanato-dehydroabiete) hexane, bi s-(12-isocyanato-dehydroabiete) octane, 1-(12-isocyanato-dehydroabietate)-n'-(14-isocyanato-dehydroabietate) octane, bis-(14-isocyanato-dehydroabiete) octane, and mixtures thereof.

11. The polyurethane elastomer of claim 8, wherein from about 85% to about 99% of the weight of the polyurethane elastomer is derived from biobased content.

12. The polyurethane elastomer of claim 8, further comprising one or more of a plasticizer, a colorant, a foaming agent, a chain extender, a bio-additive, and a polymerization catalyst.

* * * * *